US012391982B2

(12) United States Patent
Azhar et al.

(10) Patent No.: US 12,391,982 B2
(45) Date of Patent: Aug. 19, 2025

(54) OPTICAL DISCRIMINATION APPARATUS AND METHODS ADAPTED TO MONITOR REACTIONS

(71) Applicant: Siemens Healthcare Diagnostics Inc., Tarrytown, NY (US)

(72) Inventors: Mohiudeen Azhar, Bangalore (IN); Paul Patt, Walnut Creek, CA (US); Ragavendar Madrassethuraman, Sharon, MA (US); Karan Mohan, Union City, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 565 days.

(21) Appl. No.: 17/759,473

(22) PCT Filed: Feb. 17, 2021

(86) PCT No.: PCT/US2021/070159
§ 371 (c)(1),
(2) Date: Jul. 26, 2022

(87) PCT Pub. No.: WO2021/189066
PCT Pub. Date: Sep. 23, 2021

(65) Prior Publication Data
US 2023/0064409 A1 Mar. 2, 2023

Related U.S. Application Data

(60) Provisional application No. 62/990,039, filed on Mar. 16, 2020.

(51) Int. Cl.
C12Q 1/6844 (2018.01)
G01N 21/47 (2006.01)
G01N 21/64 (2006.01)

(52) U.S. Cl.
CPC ........... C12Q 1/6844 (2013.01); G01N 21/47 (2013.01); G01N 21/6428 (2013.01); C12Q 2600/16 (2013.01); G01N 2021/6421 (2013.01); G01N 2021/6439 (2013.01); G01N 2201/0634 (2013.01); G01N 2201/0635 (2013.01)

(58) Field of Classification Search
CPC .. C12Q 1/6844; C12Q 2600/16; G01N 21/47; G01N 21/6428; G01N 2021/6421; G01N 2021/6439; G01N 2201/0634; G01N 2201/0635; G01N 2021/6419; G01N 2021/6441; G01N 21/645
See application file for complete search history.

(56) References Cited

U.S. PATENT DOCUMENTS

| | | | |
|---|---|---|---|
| 5,483,075 A * | 1/1996 | Smith | G01N 27/44721 204/461 |
| 7,229,799 B2 | 6/2007 | Williams | |
| 7,586,604 B2 | 9/2009 | Sharpe et al. | |
| 9,089,828 B2 | 7/2015 | Howell et al. | |
| 9,488,571 B2 | 11/2016 | Bahatt et al. | |
| 2007/0098594 A1 | 5/2007 | Elkin et al. | |
| 2007/0109536 A1 | 5/2007 | Weiss et al. | |
| 2008/0305481 A1 | 12/2008 | Whitman et al. | |
| 2010/0167413 A1 | 7/2010 | Lundquist et al. | |
| 2011/0278475 A1 | 11/2011 | Lundquist et al. | |
| 2016/0061730 A1 | 3/2016 | Tagawa | |
| 2016/0320306 A1 | 11/2016 | Huffman et al. | |
| 2018/0011021 A1 | 1/2018 | Shoji et al. | |
| 2019/0086334 A1 | 3/2019 | Oldham et al. | |
| 2019/0177779 A1 * | 6/2019 | Whitman | C12Q 1/6834 |
| 2019/0241934 A1 | 8/2019 | Maher | |

FOREIGN PATENT DOCUMENTS

| | | |
|---|---|---|
| CN | 102342861 | 2/2012 |
| CN | 104483254 | 4/2015 |
| CN | 204269552 | 4/2015 |
| CN | 108449958 | 8/2018 |
| CN | 109030432 | 12/2018 |
| WO | 2015039425 | 3/2015 |

OTHER PUBLICATIONS

International Search Report for PCT/US2021/070159 dated Apr. 28, 2021.
Nano Life Quest, MyGo Pro RealTime PCR System website screenshot, www.nanolifequest.com/mygo-pro-realtime-pcr-system.html, downloaded Mar. 9, 2020.
D. Jang, et.al, "Miniaturized Fluorometer Based on Total Internal Reflector and Condensing Mirror" Journal of the Optical Society of Korea vol. 17, No. 1, Feb. 2013, pp. 81-85.
Maruyama et. al.,"A novel filterless fluorescence detection sensor for DNA analysis" in IEEE Transactions on Electron Devices, vol. 53, No. 3, (2006).
Booth et. al.. "Full spectrum filterless fluorescence microscopy" Journal of Microscopy, 237: 103-109. doi:10.1111/j.1365-2818.2009.03317.x (2010).

(Continued)

Primary Examiner — Narayan K Bhat

(57) ABSTRACT

An optical discrimination apparatus adapted for use in PCR testing and the like. The apparatus includes a multi-color light emitter to emit excitation light, a sample holder configured to hold dye-marked nucleic acid fragments in a PCR solution at a position configured to receive the excitation light along a first direction, light emission collection optics configured to collect scattered excitation light and light emission (fluorescent emission) from the sample holder along a second direction that is approximately orthogonal to the first direction, a spectrally-dispersive element configured to spectrally disperse scattered light and emission light, and a spectral detector configured to receive the separated emission light and excitation light on different photosites of the spectral detector. Systems and methods are provided, as are other aspects.

11 Claims, 4 Drawing Sheets

(56) References Cited

OTHER PUBLICATIONS

Noor et al., CMOS spectrally-multiplexed Fret-on-a-Chip for DNA analysis. IEEE Trans. Biomed. Circuits Syst. 2013, 7, 643-654.
Zhaonan Jing et al:; "Fluorescence spectral characteristics analysis of dissolved organic matter in wate"; Acta Photonica Sinica ;Mar. 30, 2007, English Abstract.

\* cited by examiner

OPTICAL DISCRIMINATION APPARATUS AND METHODS ADAPTED TO MONITOR REACTIONS

FIELD

This disclosure relates to optical discrimination apparatus and more particularly, to apparatus, systems, methods configured to carry out measurements of light emissions (e.g., fluorescent light) emanating from a reaction vessel containing dye-labeled nucleic acids.

BACKGROUND

In some automated optical discrimination systems, a sample container (e.g., a cuvette) containing extracted and labeled components (e.g., four nucleotides of nucleic acid strands for DNA: adenine (A), guanine (G), cytosine (C), and thymine (T)) extracted from a specimen (e.g., biological specimen) and amplified via known PCR sample preparation methods can be positioned at a desired location in an optical-based system. Thereafter, readings can be obtained of light emissions (e.g., fluorescent light) emanating from the extracted and labeled components.

Such optical discrimination systems can utilize optical components such as a white light emitting diode (LED) as a light source, one or more filters, one or more dichroic mirrors, various focusing optics, and a detection sensor. In particular, in nucleic acid sequencing to determine the nucleotide sequence of particular nucleic acid molecules, the nucleotides (AGCT) in DNA fragments may be labeled with four separate fluorescent markers in current sequencing methods. The fluorescent markers (fluorophores) are molecules that are capable of absorbing the filtered excitation light from the LED and emitting it at one or more well-defined wavelengths. The fluorescent dye markers are incorporated into the DNA strands by PCR processing and provide the extracted and labeled DNA. For example, ddATP can be labeled with a green dye; ddGTP can be labeled with a yellow dye; ddCTP can be labeled with blue; and ddTTP can be labeled with red dye. Then the sequence of the DNA can be determined by automated techniques using measured fluorescence intensity and wavelength data.

In current fluorescence-based optical discrimination systems, for each wavelength of excitation light, one or more filters and one or more dichroic mirrors are employed that pass one wavelength of light from the white spectrum, but cuts out all others. Such optical filters and dichroic mirrors tend to be expensive and quite complicated. A different filter and dichroic mirror can be used, such as provided on a rotating filter wheel or translation stage for each separate wavelength of emitted excitation light from the white light LED, so as to enable excitation of different colors of fluorescent dyes. For example, to discriminate four different dyes, generally four different filters and/or dichroic mirrors are used. Hence, the complication and expense of these prior art optical interrogation systems is relatively high.

SUMMARY

In some embodiments, an optical discrimination apparatus is provided. The optical discrimination apparatus includes a multi-color light emitter configured to emit excitation light, a sample holder configured to hold extracted dye-marked nucleic acid fragments from a biological sample, located at a position configured to receive the excitation light emitted from the multi-color light emitter along a first direction, light emission collection optics configured to collect scattered light and emission light from the sample holder along a second direction that is approximately orthogonal to the first direction, a spectrally-dispersive element configured to spectrally disperse the scattered light and the emission light into dispersed light spectra, and a spectral detector configured to receive at least some of the dispersed light spectra wherein the spectral detector is configured to receive at least some of the emission light and some of the excitation light on different photosites of the spectral detector.

In some embodiments, a multiplexed optical discrimination system for fluorescence detection in polymerase chain reaction testing is provided. The multiplexed optical discrimination system includes a multi-color light emitter configured to individually emit multiple wavelengths of excitation light at multiple central wavelengths, a sample holder configured to hold extracted dye-marked nucleic acid fragments from a biological sample, the sample holder located at a position configured to receive the excitation light emitted from the multi-color light emitter along a first direction, light emission collection optics configured to collect scattered light and emission light from the sample holder along a second direction that is approximately orthogonal to the first direction, a spectrally-dispersive element configured to spectrally disperse at least a portion of the scattered excitation light and the emissions light into the spectral detector, and a controller comprising a memory storing executable instructions, the executable instructions including instructions to: cause the multi-color light emitter to emit the excitation light at single central wavelength, receive signals representative of the emission light on first photosites of the spectral detector, and receive signals representative of the scattered light on second photosites of the spectral detector. The scattered light is scattered excitation light and the emission light comprises fluorescent light emissions.

In some embodiments, a method of multiplexed optical discrimination for fluorescence detection in polymerase chain reaction testing is provided. The method includes illuminating along a first direction, extracted dye-marked nucleic acid fragments from a biological sample held in a sample holder, with a excitation light emitted from a multi-color light emitter, collecting, with collection optics, excitation light and emission light emanating from the sample holder along a second direction that is approximately orthogonal to the first direction, spectrally dispersing, with a spectrally-dispersive element, at least a portion of the scattered light and at least a portion of the emission light into dispersed light spectra comprising emission light and excitation light, and receiving, at a spectral detector having a plurality of photosites, the dispersed light spectra so that various wavelengths associated with the emission light contact first photosites and various wavelengths associated with the excitation light contact second photosites.

Numerous other aspects are provided in accordance with these and other aspects of the disclosure. Other features and aspects of the present disclosure will become more fully apparent from the following detailed description, the claims, and the accompanying drawings.

DETAILED DESCRIPTION

In view of the above expressed issues and concerns, systems, methods, and apparatus that have relatively lower cost and/or complexity are desired. Further, such above-described systems are difficult to adapt to new dye colors that may fluoresce at different wavelengths, generally requiring different filters therefor. Thus, systems and apparatus that are readily adaptable to use of a new fluorescent dye that are configured to fluoresce at any new wavelength would be desirable.

In a first aspect, systems and apparatus are provided that can be implemented without any filters or dichroic mirrors. Thus, filter-less optical detection methods and apparatus adapted to detect fluorescence of multiple fluorophores is provided. Thus, advantageously, fewer components and complexity can be used resulting in relatively lower cost and lower complexity. Further, systems and apparatus with no moving parts can be implemented. In particular, systems and apparatus enabling use of a multitude of desired dyes, as well as apparatus and systems that are future-proofed are provided. Moreover, very low limits of detection can be obtained.

The systems and apparatus described herein can be filter-less, thus eliminating expensive components. Further, the systems can include multiple different wavelength light sources that can be individually excited to produce different colors of excitation light. Further, the excitation of different fluorescent dyes can be accomplished with no change to the structure of the apparatus, (e.g., no changing of filters and/or dichroic mirrors) as in the prior art, other than the addition of the light emitter adapted to emit the new color of excitation light. In particular also, the relative ratio of excitation intensity Ee to fluorescence emission intensity Ef at the detector tends to be quite low, whereas the ratio Ee/Ef in the prior art can be as high as 1,000,000:1. Thus, signal-to-error ratio can be dramatically improved.

Figure 1:
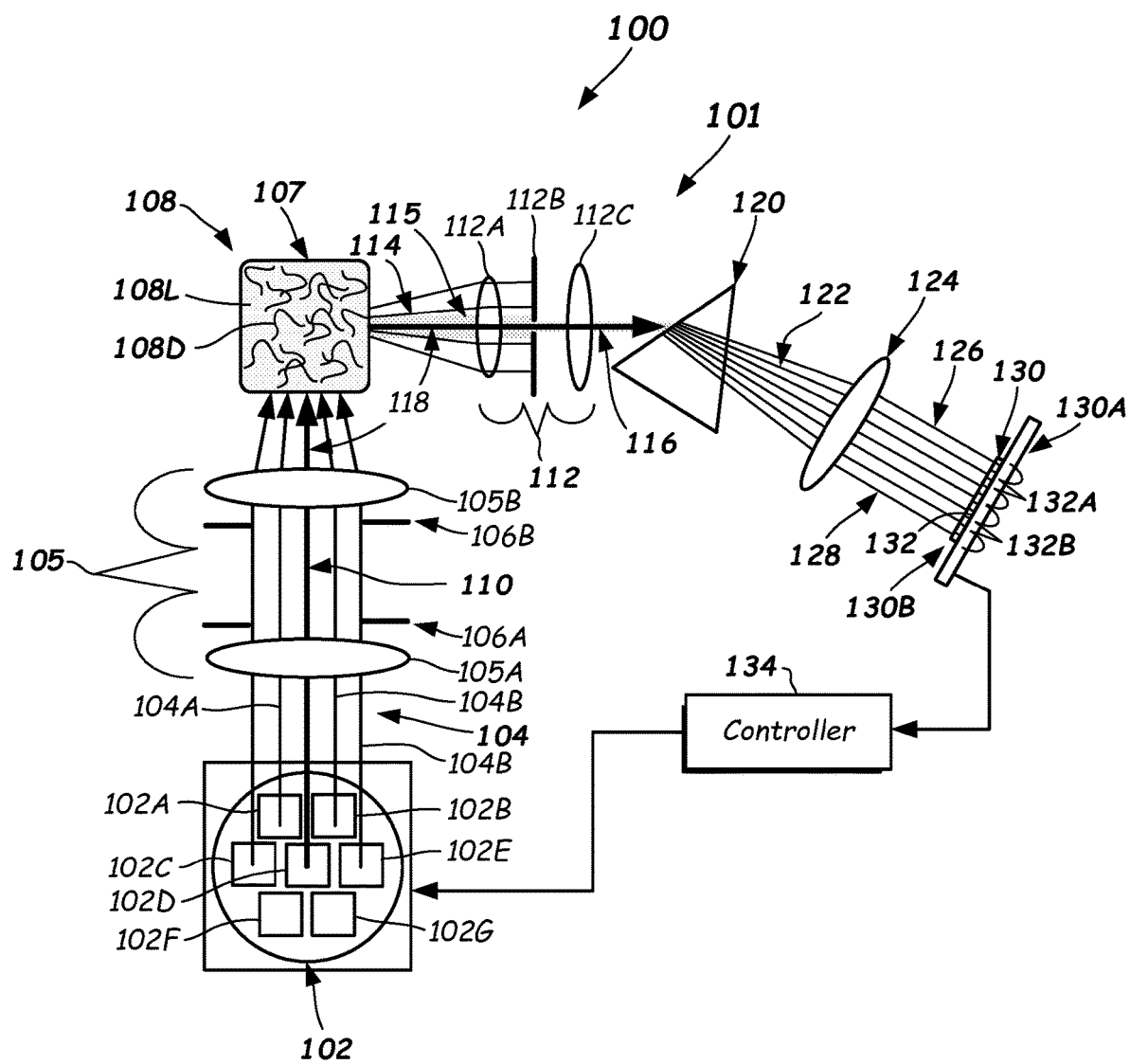
FIG. 1 is a schematic diagram of an optical discrimination apparatus according to embodiments of the present disclosure.
Figure 2A:
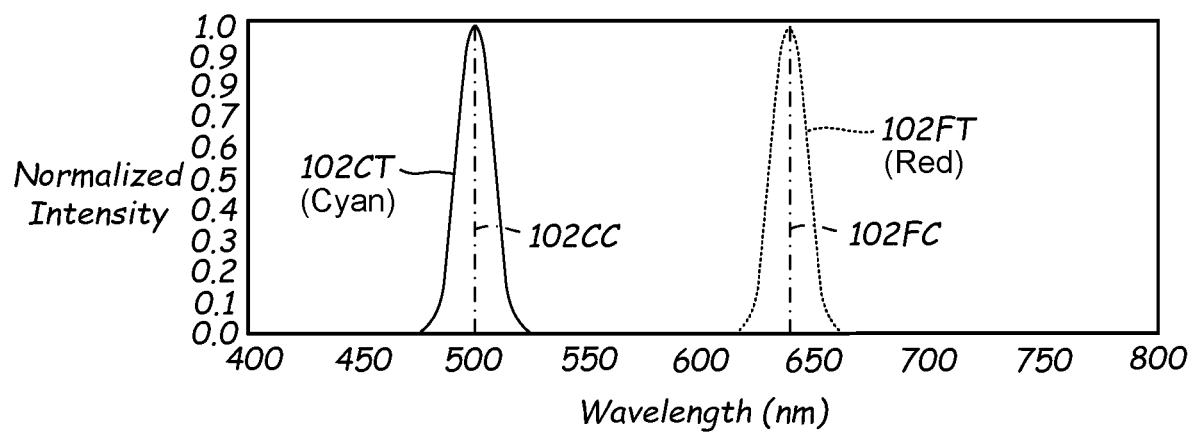
FIG. 2A is a spectral plot of two example colors of excitation light (Cyan and Red) from a multi-color light emitter according to embodiments of the present disclosure.
Figure 2B:
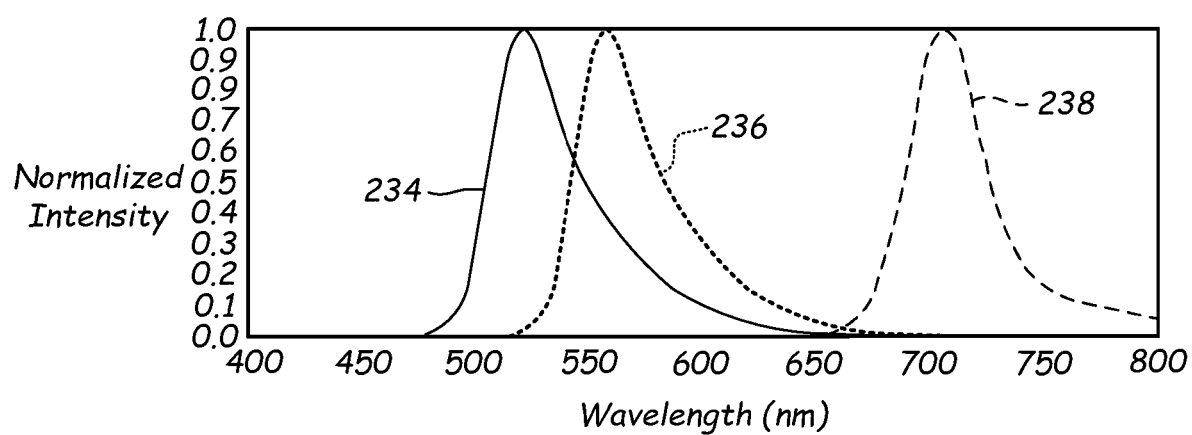
FIG. 2B is a spectral plot of emission light spectra for three different dyes that are tagged to the nucleic acid fragments according to embodiments of the present disclosure.
Figure 2C:
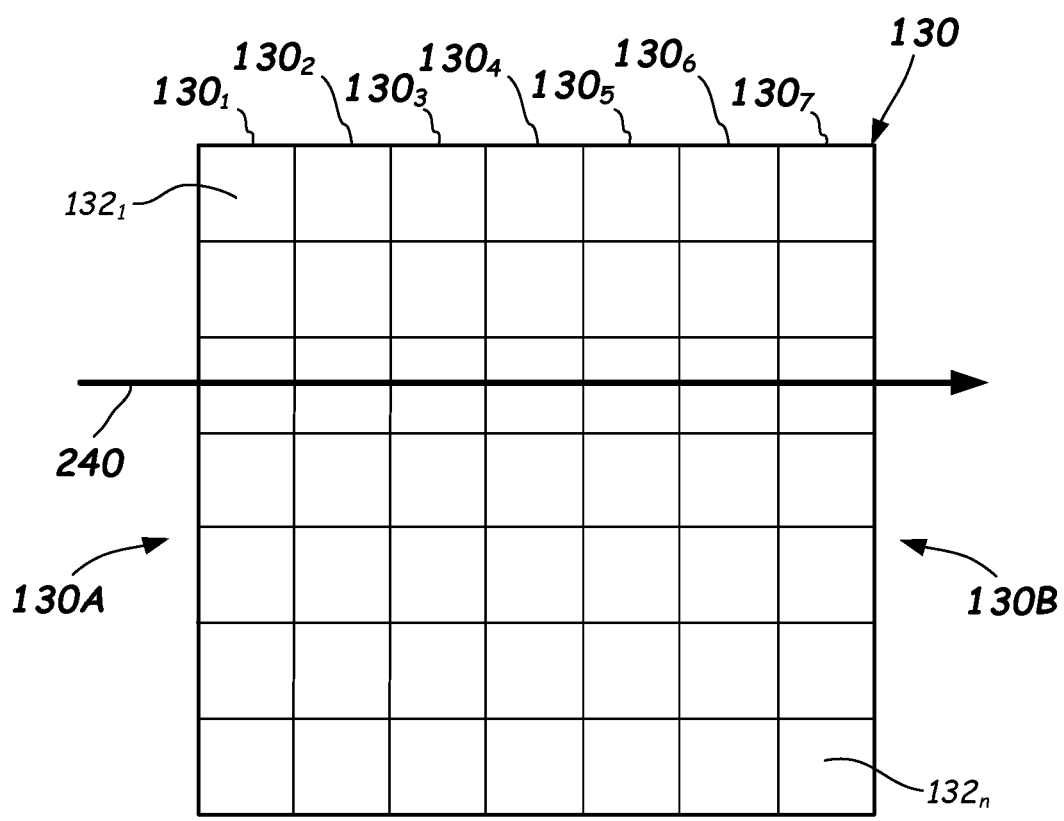
FIG. 2C is a plan view of a spectral detector configured to collect scattered excitation light and emission light that have been spectrally-separated according to embodiments of the present disclosure.
Figure 3:
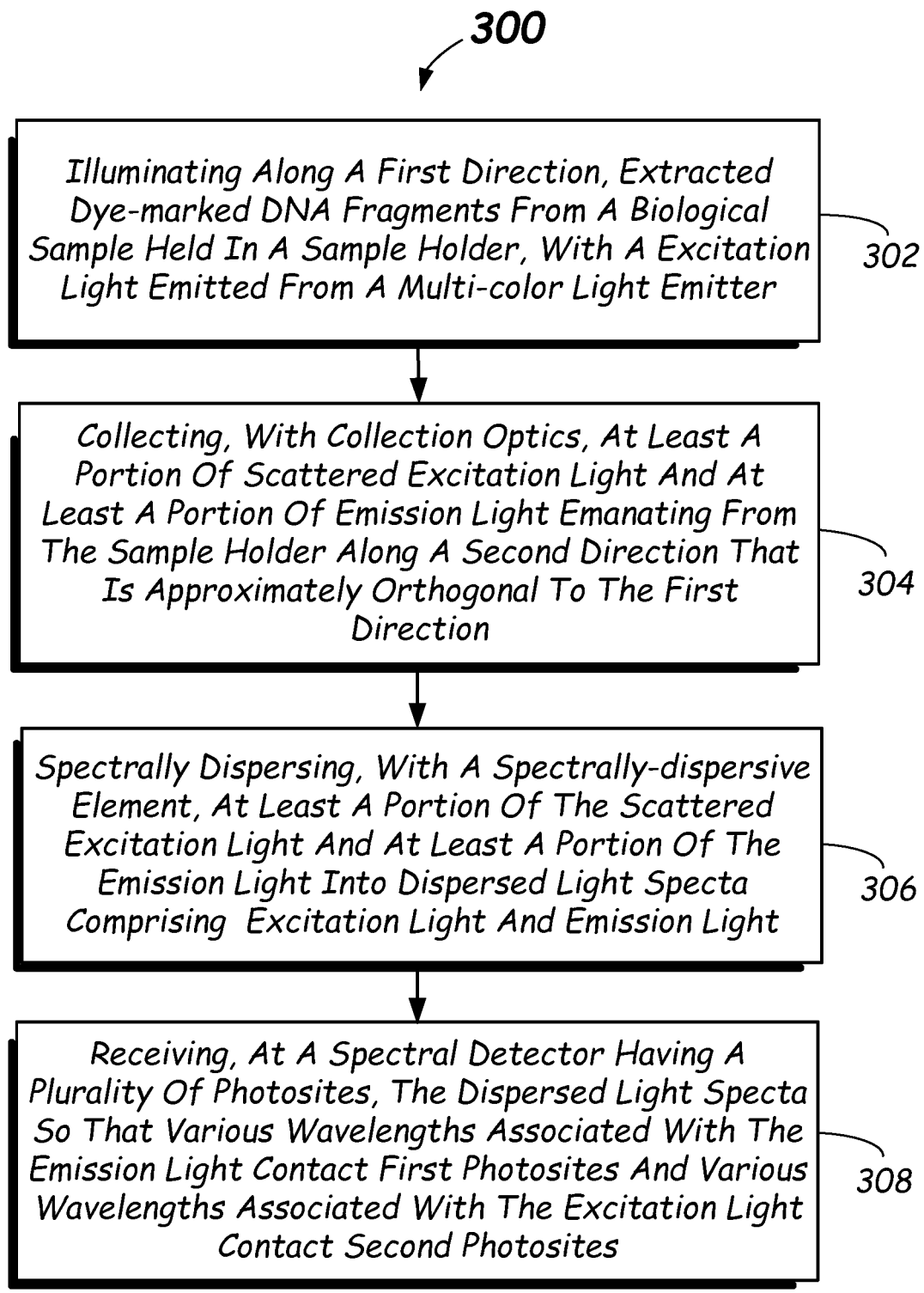
FIG. 3 is a flowchart depicting an example method of multiplexed optical discrimination for fluorescence detection in polymerase chain reaction (PCR) testing according to embodiments of the present disclosure.

Further details and examples of apparatus, systems, and methods of the disclosure are provided in FIGS. 1-3 herein.

FIG. 1 depicts an example embodiment of an optical discrimination system 100 adapted to measure intensities and wavelengths of fluorescence (fluorescent emissions) of multiple dyes tagged to nucleic acid strands 108D of a sample contained in a sample holder 107 at a sample location 108. The optical discrimination system 100 includes and optical discrimination apparatus 101 controlled by a suitable controller 134.

In more detail, the optical discrimination apparatus 101 comprises a multi-color light emitter 102, a sample holder 107, light emission collection optics 112, a spectrally-dispersive element 120, and spectral detector 130. Other optical components may be present in the optical discrimination apparatus 101, as will be apparent from the following.

Optical discrimination apparatus 101 comprises a multi-color light emitter 102 that can be configured to emit excitation light 104 at more than one color at more than one distinct wavelength ranges. For example, as shown, multi-color light emitter 102 can comprise seven individual light sources 102A-102G, six of which are configured to emit light at an individual predominant peak wavelength $\lambda_0$. The individual predominant wavelength (peak) for each is designated as a central wavelength $\lambda_0$, but it should be understood that each of the individual colored light sources 102A-102F will produce a distinct narrow spectral range about their central wavelength $\lambda_0$. White light may have multiple peaks and a quite broad range.

For example, as shown below in FIG. 2A, an individual light source 102C (Cyan) may emit a particular color signature or trace 102CT of normalized intensity versus wavelength (nm). The trace (e.g., 102CT) will include the central wavelength $\lambda_0$ (peak) 102CC, in this case located at approximately 500 nm, yet the spectral distribution of normalized intensity will comprise a distribution about the central wavelength 102CC such as is shown, for example, such as a normal or slightly non-normal distribution. The other light sources 102A-102B and 102D-102F) may emit light as shown in Table 1. Each has a central wavelength $\lambda_0$ (peak) and a narrow spectral range about the central wavelength $\lambda_0$. Thus, each color can be emitted from the light emitter 102, independently. Red colored light source trace 102FT is shown with its corresponding central wavelength $\lambda_0$ 102FC.

TABLE 1

| | Example light sources | | |
|---|---|---|---|
| Trace | Color | Approx. Central Wavelength (nm) | Approx. Wavelength Range (nm) |
| 102AT | Violet | 405 | 370-450 |
| 102BT | Blue | 450 | 420-490 |
| 102CT | Cyan | 500 | 450-550 |
| 102DT | Green | 543 | 475-575 |
| 102ET | Amber | 576 | 550-620 |
| 102FT | Red | 633 | 590-660 |
| 102GT | Cool White | 430 and 570 | 400-800 |

Although seven individual light sources are shown in Table 1, more or less number of individual light sources can be used, and different central wavelengths $\lambda_0$ may be used depending upon the particular dye being used and its excitation characteristics. Individual light sources may be paired with particular dyes being used for excitation thereof. Individual light sources can be light emitting diodes (LEDs), for example. The multi-color light emitter 102 may include multiple different colored LEDs and may also include a flat lens in some embodiments.

In some embodiments, the multi-color light emitter 102 can output red, amber, green, cyan, blue, and violet. The the multi-color light emitter 102 can also emit white light, which may be used for system calibration or other purposes. However, any suitable combination of colors can be used, depending on the particular series of dyes that are tagged to the nucleic acid strands 108D. DNA as used herein is used to denote deoxyribonucleic acid. However_, the present invention is equally applicable to ribonucleic acid (RNA).

The term nucleic acid denotes DNA and RNA, and, thus, analysis of either DNA or RNA may be undertaken by using the present disclosure.

In some embodiments, the multi-color light emitter 102 may be a LZ7 series LUXIGEN™ available from LED ENGIN of San Jose, CA Other suitable types of the multi-color light emitter 102 can be used.

Optical discrimination apparatus 101 further includes a sample holder 107, configured to hold extracted dye-marked nucleic acid fragments 108D in a PCR solution that have been obtained (extracted in eluate) from a biological sample, such as bodily fluid (e.g., serum, plasma, urine, and the like). The sample holder 107 can be a cuvette or other vessel that is optically transparent or translucent, such as a plastic or glass. The walls of the sample holder 107 may be planar or can be curved or combinations thereof.

The dye-marked nucleic acid fragments 108D are provided in a suitable liquid 108L, such as a PCR liquid including, for example, a solution of eluate, PCR master mix, and primer (or probe), and possibly a reagent and/or deionized water. The sample holder 107 is located at a position 108 configured to receive the excitation light 104 emitted from the multi-color light emitter 102 along a first direction 110. The excitation light 104 can be provided from any one of the multiple individual light sources (e.g., light sources 102A-102G). The multi-color light emitter 102 can be a multi-color emitter configured to emit multiple colors of light having central wavelengths $\lambda_0$ ranging from 350 nm to 700 nm. Multi-color light emitter 102 may optionally include the capability of emitting white light.

Drive signals from controller 134 to a particular one of the light sources 102A-102G can be provided to cause the illumination and emission of the excitation light 104 therefrom. The multi-color light emitter is a capable of emitting at least three individual colors of light. For example, red (R), Green (G) and Blue (B) can be used. Other numbers of light sources can be used, such as 4 or more individual light sources, such as 5 or more individual light sources, such as 6 or more individual light sources, or even such as 6 or more individual light sources coupled with a white light source.

Optical discrimination apparatus 101 may further include collimating components 105. Collimating components 105 can include collimating lens 105A, focusing lens 105B to concentrate light intensity into the sample location 108, and apertures 106A, 106B. The apertures 106A, 106B prevent the divergent light from the various individual sources of the multi-color light emitter 102 from being exposed to the sample location 108, and thereby allowing the central collimated light beam in the first direction 110 through to the into the sample location 108.

Optical discrimination apparatus 101 may further include light emission collection optics 112 configured to collect scattered light 114 and emission light 115 emanating from the sample holder 107 along a second direction 116 that is approximately orthogonal (collection angle 118) to the first direction 110. By approximately orthogonal it is meant that the second direction 116 is oriented at a collection angle 118 of from 70 degrees to 110 degrees, or even from 80 degrees to 100 degrees, in relationship to the first direction 110.

Optical discrimination apparatus 101 may further include a spectrally-dispersive element 120 that may be configured to spectrally disperse at least a portion of the scattered light 114 and emission light 115 into dispersed light spectra 122 comprising emission light and excitation light. Emission light 115 may be confined predominantly to one end of the spectrum, while excitation light may be confined predominantly to the other end of the spectrum. The spectrally-dispersive element 120 can be a prism (e.g., a triangular prism), or optionally a diffraction grating, although a diffraction grating may have more optical losses.

Optical discrimination apparatus 101 may further include a focusing lens 124 that may be configured to focus the dispersed light spectra 122 onto the spectral detector 130. Any suitable focusing lens or combination of lenses may be used.

Optical discrimination apparatus 101 may further include the spectral detector 130 configured to receive at least some of the dispersed light spectra 122 wherein the spectral detector 130 is configured to receive at least some of the emission light 126 and at least some of the excitation light 128 on different photosites $132_1$ through $131_n$ of the spectral detector 130. The different photosites $132_1$ through $131_n$ of the spectral detector 130 can be arranged as shown in FIG. 2C, wherein columns $130_1$ through $130_7$ are arranged from a first side 130A of the spectral detector 130 to a second side 130B of the spectral detector 130. The spectral detector 130 is an optical sensor (e.g., a sensor array) and may be a CCD device (e.g., monochrome CCD camera), CMOS device, or the like.

Spectral detector 130 can comprise a plurality of different photosites $132_1$ through $132_n$ and the spectrally-dispersive element 120 separates various wavelengths of light so that the wavelengths of light that are emission light 126 contact different ones of the plurality of photosites as compared to the scattered excitation light 128. For example, emission light 126 can contact a first group 132A of the photosites, that are arranged in columns $130_1$ through $130_7$ and the scattered light 128 can contact a second group 132B of the photosites 132 arranged in columns $130_1$ through $130_7$.

Data signals from the spectral detector 130 may be communicated to the controller 134, which processes them to detect at least the portions of the signals that relate to the emission light 126. Thus, for any particular excitation input from the multi-color light emitter 102, the scattered light 128 can be discriminated from the emission light 126 and respective data can be obtained. FIG. 2B, for example, illustrates the emissions plots 234, 236, 238 of normalized intensity versus wavelength (in nm) for each of three different example dyes. For example, the trace of a first dye 234 can be for FAM dye; trace of a second dye 236 can be for CAL Fluor Orange 560 dye; and trace of a third dye 238 can be for Quasar 705 dye. Pixel intensities across one or more rows of the spectral detector 130 can be recorded. Row is signified by arrow 240. Each column $130_1$-$130_7$ may include hundreds of pixels. Each pixel along the row corresponds to a discreet wavelength or small wavelength range. Thus, by recording the emission responses to particular color excitation inputs, the particular dyes present can be determined, as well as magnitudes thereof. For example, excitation with 102CT (cyan) as shown in FIG. 2A causes emission light 126 to be received at the detector 130 and fluorescence traces 234 and 236 can be reconstructed therefrom via multiplexing method described herein based upon measured magnitude of light intensity as a function of wavelength. Likewise, excitation with red source 102FT in FIG. 2A causes emission light 126 to be received at the detector 130 and fluorescence trace 238 can be reconstructed from the detector readings via the multiplexing method herein.

In one aspect, the optical discrimination apparatus 101 is devoid of any optical filter, i.e., the optical discrimination apparatus 101 does not contain any filters therein. As such, the system 101 is much more adaptable and multiple input wavelengths can be used as individual excitation light inputs in rapid succession, without having to change out a filter or dichroic mirror as in the prior art. Thus, not only can the optical discrimination apparatus 101 be manufactured for relatively less cost, because the emission light 126 is captured orthogonally to the first direction 110 of the exciting light 104, the overall level of intensity of the scattered excitation light 128 is less, so that on a relative basis, the ratio of emissions light 126 to the excitation light 128 is made larger as compared to prior art systems, thus the signal-to-noise ratio is advantageously made greater.

In another embodiment, the present disclosure is directed at a multiplexed optical discrimination system 100 for fluorescence detection in polymerase chain reaction testing. The multiplexed optical discrimination system 100 comprises the multi-color light emitter 102 configured to individually emit multiple wavelengths of excitation light 104 at multiple emission wavelengths (e.g., at individual central wavelengths $\lambda_0$ from 350 nm to 700 nm), and possibly also white light.

The multiplexed optical discrimination system 100 also includes a sample holder 107 configured to hold extracted dye-marked nucleic acid fragments 108D from a biological sample, the sample holder 107 located at a position configured to receive the excitation light 104 emitted from the multi-color light emitter 102 along a first direction 110.

Additionally, the multiplexed optical discrimination system 100 includes light emission collection optics 112 that are configured to collect scattered excitation light 114 and fluorescent emissions 115 emanating from the sample holder 107 along the second direction 116 that is approximately orthogonal to the first direction 110.

A spectrally-dispersive element 120 of the multiplexed optical discrimination system 100 is configured to spectrally disperse at least a portion of the scattered excitation light 114 and of the emissions light 115 (e.g., florescent emissions) into dispersed light spectra 122 comprising emission light 126 and excitation light 128, which are separated.

The spectral detector 130 of the multiplexed optical discrimination system 100 is configured to receive at least some of the dispersed light spectra 122 wherein the spectral detector 130 is configured to receive at least some of the emission light 122 and some of the excitation light 126 on a plurality of different photosites $132_{1-n}$ of the spectral detector 130.

The controller 134 of the multiplexed optical discrimination system 100 can comprise a memory storing executable instructions, and the executable instructions can include instructions to: cause the multi-color light emitter 102 to emit the excitation light 104 at single central wavelength $\lambda_0$ of one of the non-white light sources from multi-color light emitter 102, and receive signals representative of the emission light 126 on a first group of photosites 132A of the spectral detector 130, and receive signals representative of the excitation light 128 on second group of photosites 132B of the spectral detector 130.

The multiplexed optical discrimination system 100 can be calibrated by using white light. Pixels of the spectral detector 130 can be calibrated to their corresponding spectral wavelength. A milky scattering medium (e.g., intralipid 20%) can be used in the sample holder 107 in order to facilitate scattering of the white light emitted from the multi-color light emitter 102. The spectrally-dispersive element 120 (e.g., prism) then projects the "rainbow" (e.g., the spectrally-dispersed white light) onto different pixels on the group of photosites 132A, 132B of the spectral detector 130. The locations of the individual colored LEDS (e.g., 405 nm (violet), 450 nm (blue), 500 nm (cyan), 543 nm (green), 576 nm (amber), and 633 nm (red) respectively) can be individually lighted to note the different colors are resolved at spatially-separated pixels on the groups of photosites 132A, 132B of the spectral detector 130. This calibration can be used to assign pixels on the photosites 132A, 132B to their corresponding wavelengths by using the excitation LEDs or by white light LED with narrow band filters (about 10 nm) at various wavelengths between 400-800 nm. Pixel intensity averages for each pixel of the photosites 132A, 132B along the row 240 corresponding to the emission wavelengths can be used in calibrating the system 100 with various concentrations of dyes to obtain the emission coefficient matrix for the multiplexing method.

FIG. 3 illustrates a flowchart depicting a method 300 of multiplexed optical discrimination for fluorescence detection in polymerase chain reaction (PCR) testing. The method 300 comprises, in block 302, illuminating along a first direction 110, dye-marked nucleic acid fragments 108D (in the PCR fluid) held in a sample holder 107 that were extracted from a biological sample, with a excitation light 104 (e.g., a single central wavelength $\lambda_0$ of light) emitted from a multi-color light emitter 102. The excitation light 104 emitted may be an individual single color (e.g., Red), which may be followed in rapid sucession by excitation light 104 emitted at other colors (e.g., in sucession red, amber, green, cyan, blue, and violet, for example). Other colors may be used to excite other dyes in addition or in substitution for the foregoing. Several dyes and their corresponding excitation color are shown below in Table 2.

TABLE 2

| Dyes and associated excitation colors | |
| --- | --- |
| Dye | Color |
| Quasar 705 | Red |
| Quasar 670 | Red |
| Pulsar 650 | Red |
| Cy5 | red |
| Texas Red | Amber |
| FAM | Blue |
| VIC | Cyan |
| JOE | Cyan |
| CAL Fluor Orange 560 | Cyan |

The method 300 further includes, in 304, collecting, with collection optics 112, scattered excitation light 114 and emission light 115 (e.g., fluorescent emissions) emanating from the sample holder 107 along a second direction 116 that is approximately orthogonal to the first direction 110. The term "approximately" is defined the same as above.

In block 306, the method 300 includes spectrally dispersing, with a spectrally-dispersive element 120 (e.g., prism or grating), at least a portion of the scattered light 114 and at least a portion of the emission light 115 into dispersed light spectra 122 comprising emission light 126 and excitation light 128.

In block 306, the method 300 includes receiving, at a spectral detector 130 having a plurality of photosites $132_{1-n}$, the dispersed light spectra 122 so that various wavelengths associated with the emission light 126 contact a first group of photosites 132A and various wavelengths associated with the excitation light 128 contact a second group of photosites 132B. The photosites 132A, 132B may contain hundreds of pixels.

Following provision of the dispersed emission light 126 to the first group of photosites 132A and various wavelengths of dispersed light associated with the excitation light 128 to the second group of photosites 132B, the corresponding intensity values of pixels at photosites 132A, 132B of at least the emissions light 126 at each excitation wavelength is collected by the controller 134. This data may be analyzed through matrix calculations to obtain responses to the applied excitation light 104, which may comprise one or more emission peaks.

In particular, the data can be analyzed using a multiplexing method that has been trained using calibration training sets for each dye to be used with different concentrations, such as 1.25 nM, 2.5 nM, 5 nM, 10 nM, 50 nM, and 100 nM, for example. Other suitable increasing nanomolar concentrations may be used. Pixel intensity averages for each pixel or photosites 132A, 132B across a pixel row from the spatial detector 130 can be obtained for each known concentration of each dye (Dye Concentration). From this data an emission coefficient matrix can be obtained as shown below using matrix algebra.

Pixel Intensity Average  Emission Coeffient Matrix  Dye Concentration $$\begin{bmatrix} Intensity_{pixel1} \\ Intensity_{pixel2} \\ Intensity_{pixel3} \end{bmatrix} \begin{bmatrix} EM_{FAM1} & EM_{CAL1} & EM_{QUS1} \\ EM_{FAM2} & EM_{CAL2} & EM_{QUS2} \\ EM_{FAM3} & EM_{CAL3} & EM_{QUS3} \end{bmatrix} \begin{bmatrix} Conc_{FAM} \\ Conc_{CAL} \\ Conc_{QUS} \end{bmatrix}$$

Fluorescence emissions (emission light 126) and excitation residue from scattered excitation light 128 can easily be discriminated as they occur at different locations on the photosites 132A, 132B of the spatial detector 130, as determined by calibration with known dye concentrations. After sequentially exciting the sample holder 107 with the different colored lights and recording the emissions intensity responses thereto per pixel, the known emissions coefficient matrix constructed from the calibration can be used to determine the concentrations for each of the dyes present. Thus, the present disclosure allows multiplexing and determination of the concentrations of the particular dye-tagged nucleic acid components when multiple dyes are present.

Although the embodiments are described herein with reference to specific examples, the scope of the disclosure is not intended to be limited to the details and specific examples described herein. Rather, various modifications may be made to the embodiments and details within the scope and range of equivalents of the claims.

What is claimed is:

1. An optical discrimination apparatus, comprising:
   a multi-color light emitter configured to emit excitation light;
   a sample holder, configured to hold extracted dye-marked nucleic acid fragments from a biological sample, located at a position configured to receive the excitation light emitted from the multi-color light emitter along a first direction;
   light emission collection optics configured to collect scattered light and emission light from the sample holder along a second direction that is approximately orthogonal to the first direction;
   a spectrally-dispersive element configured to spectrally disperse the scattered light and the emission light into dispersed light spectra; and
   a spectral detector configured to receive at least some of the dispersed light spectra wherein the spectral detector is configured to receive at least some of the excitation light and at least some of the emission light on different photosites of the spectral detector.

2. The optical discrimination apparatus of claim 1, wherein the multi-color light emitter is configured to emit multiple colors of light each having a dominant wavelength $\lambda_0$ ranging from 350 nm to 700 nm.

3. The optical discrimination apparatus of claim 1, wherein the multi-color light emitter is configured to emit six colors of light wherein the dominant wavelength $\lambda_0$ of individual emitters is approximately 405 nm, 450 nm, 500 nm, 543 nm, 576 nm, and 633 nm.

4. The optical discrimination apparatus of claim 1, wherein the multi-color light emitter is a capable of emitting at least three individual colors of light.

5. The optical discrimination apparatus of claim 1, wherein the spectral detector is an optical sensor comprising a plurality of photosites and the spectrally-dispersive element separates various wavelengths of light so that the various wavelengths of light contact different ones of the plurality of photosites.

6. The optical discrimination apparatus of claim 1, wherein the spectrally-dispersive element is a prism.

7. The optical discrimination apparatus of claim 1, wherein the spectrally-dispersive element is a grating.

8. The optical discrimination apparatus of claim 1, wherein the optical discrimination apparatus is devoid of any optical filter.

9. The optical discrimination apparatus of claim 1, wherein the second direction is oriented at a collection angle of from 70 degrees to 110 degrees in relationship to the first direction.

10. A multiplexed optical discrimination system for fluorescence detection in polymerase chain reaction testing, comprising:
    a multi-color light emitter configured to individually emit multiple wavelengths of excitation light at multiple emission wavelengths;
    a sample holder configured to hold extracted dye-marked nucleic acid fragments from a biological sample, the sample holder located at a position configured to receive the excitation light emitted from the multi-color light emitter along a first direction;
    light emission collection optics configured to collect scattered excitation light and fluorescent emissions emanating from the sample holder along a second direction that is approximately orthogonal to the first direction;
    a spectrally-dispersive element configured to spectrally disperse at least a portion of the scattered excitation light and the fluorescent emissions into dispersed light spectra comprising emission light and excitation light;
    a spectral detector configured to receive at least some of the dispersed light spectra wherein the spectral detector is configured to receive at least some of the emission light and some of the excitation light on different photosites of the spectral detector; and
    a controller comprising a memory storing executable instructions, the executable instructions including instructions to:
    cause the multi-color light emitter to emit the excitation light at a single emission wavelength, and
    receive signals representative of the emission light on first group of photosites of the spectral detector, and
    receive signals representative of the excitation light on second group of photosites of the spectral detector.

11. A method of multiplexed optical discrimination for fluorescence detection in polymerase chain reaction testing, comprising:

illuminating along a first direction, extracted dye-marked nucleic acid fragments from a biological sample held in a sample holder, with a excitation light emitted from a multi-color light emitter;

collecting, with collection optics, scattered excitation light and emissions light emanating from the sample holder along a second direction that is approximately orthogonal to the first direction;

spectrally dispersing, with a spectrally-dispersive element, at least a portion of the scattered excitation light and at least a portion of the emissions light 115 into dispersed light spectra comprising emission light 126 and excitation light; and receiving, at a spectral detector having a plurality of photosites, the dispersed light spectra so that various wavelengths associated with the emission light contact a first group of photosites and various wavelengths associated with the excitation light contact a second group of photosites.

* * * * *